United States Patent [19]

Huser et al.

[11] Patent Number: 5,486,643
[45] Date of Patent: Jan. 23, 1996

[54] ISOMERIZATION OF 2-METHYL-3-BUTENENITRILE

[75] Inventors: Marc Huser, Villeurbanne; Robert Perron, Charly, both of France

[73] Assignee: Rhone-Poulenc Chimie, Courbevoie Cedex, France

[21] Appl. No.: 321,111

[22] Filed: Oct. 11, 1994

[30] Foreign Application Priority Data

Oct. 8, 1993 [FR] France ................................ 93 12320

[51] Int. Cl.$^6$ ................................................ C07C 253/30
[52] U.S. Cl. ................................................ 558/355
[58] Field of Search ................................ 558/355

[56] References Cited

U.S. PATENT DOCUMENTS

| | | | |
|---|---|---|---|
| 3,536,748 | 10/1970 | Drinkard, Jr. et al. | 558/338 |
| 3,579,560 | 5/1971 | Drinkard, Jr., et al. | 558/355 |
| 3,676,481 | 7/1972 | Chia | 558/338 |
| 3,697,578 | 10/1972 | Pasquino et al. | 558/355 |
| 3,739,011 | 6/1973 | Drinkard, Jr. | 558/355 |
| 3,852,329 | 12/1974 | Tomlinson | 558/355 |
| 3,853,948 | 12/1974 | Drinkard, Jr. et al. | 558/355 |
| 4,087,452 | 5/1978 | Kuntz | 558/338 |
| 4,298,546 | 11/1981 | McGill | 558/355 |

FOREIGN PATENT DOCUMENTS

| | | |
|---|---|---|
| 2033107 | 11/1970 | France . |
| 2073605 | 10/1971 | France . |
| 2136815 | 12/1972 | France . |
| 2338253 | 8/1977 | France . |

Primary Examiner—Joseph Paul Brust
Attorney, Agent, or Firm—Burns, Doane, Swecker & Mathis

[57] ABSTRACT

2-Methyl-3-butenenitrile is efficiently and readily converted into a linear pentenenitrile, notably 3-pentenenitrile, a valuable intermediate for the production of adiponitrile, by isomerizing same in the presence of a catalytically effective amount of an aqueous solution of at least one sulfonated phosphine and at least one transition metal compound.

18 Claims, No Drawings

ISOMERIZATION OF 2-METHYL-3-BUTENENITRILE

BACKGROUND OF THE INVENTION

1. Field of the Invention

The present invention relates to the isomerization of 2-methyl-3-butenenitrile into linear pentenenitriles, in particular into 3-pentenenitrile.

2. Description of the Prior Art

During the hydrocyanation of butadiene, in the presence of a nickel-based catalyst and an aryl phosphite co-catalyst, as described in U.S. Pat. No. 3,496,215, in addition to the 3-pentenenitrile target compound, a large amount of 2-methyl-3-butenenitrile is formed.

The latter compound cannot be directly used for the preparation of adiponitrile, one of the basic starting materials for the preparation of polyamide 66.

However, the amounts of this byproduct are so great, taking account of the vast tonnage of adiponitrile produced, that it is inconceivable to simply discard same to waste.

Also, it has long been a desideratum in this art to isomerize 2-methyl-3-butenenitrile into 3-pentenenitrile, an adiponitrile intermediate.

Thus, U.S. Pat. No. 3,536,748 describes converting 2-methyl-3-butenenitrile into linear pentenenitrile, by contacting same with a nickel-based catalyst of oxidation state 0, such as a tetrakis(alkyl or aryl phosphite)nickel, at a temperature of 10° to 200° C.

From the results obtained employing this isomerization process, it is observed that the percentage of linear pentenenitrile produced is very low, generally ranging from 0.4% to approximately 14% according to the examples of the patent, even though the reaction is carried out for several hours.

U.S. Pat. No. 3,676,481 describes an improvement to the above isomerization process, by using a promoter for the nickel catalyst, i.e., either a boron derivative or a salt of a metal of Groups Ib, IIb, IIIa, IIIb, IVa, IVb, Vb, VIb, VIIb and VIII of the Periodic Table, in particular the halides of these metals. This reaction is carried out in a homogeneous organic phase, which makes the separation of the reaction products and the catalyst difficult insofar as the recycling of the catalyst is concerned, which is always desirable.

SUMMARY OF THE INVENTION

Accordingly, a major object of the present invention is the provision of an improved, simple and practical process for the isomerization of 2-methyl-3-butenenitrile into linear pentenenitrile and, more particularly, into 3-pentenenitrile.

Briefly, the present invention features a process for the isomerization of 2-methyl-3-butenenitrile into a linear pentenenitrile, comprising conducting said isomerization reaction in the presence of an aqueous solution:

(a) of at least one sulfonated phosphine of the general formula (I):

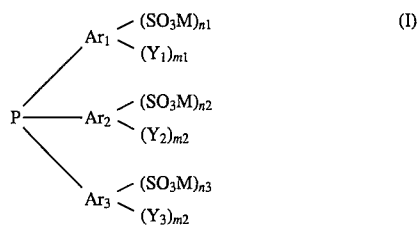

in which $Ar_1$, $Ar_2$ and $Ar_3$, which may be identical or different, are each an aryl radical; $Y_1$, $Y_2$ and $Y_3$, which may be identical or different, are each an alkyl radical having from 1 to 4 carbon atoms, an alkoxy radical having from 1 to 4 carbon atoms, a halogen atom, a CN radical, an $NO_2$ radical, an OH radical, or a radical $NR_1R_2$, in which $R_1$ and $R_2$, which may be identical or different, are each an alkyl radical having from 1 to 4 carbon atoms; M is an inorganic or organic cation selected such that the compound of formula (I) is water-soluble, from among $H^+$, cations derived from alkali metals or alkaline earth metals, $N(R_3R_4R_5R_6)_+$ in which $R_3$, $R_4$, $R_5$ and $R_6$, which may be identical or different, are each an alkyl radical having from 1 to 4 carbon atoms, or a hydrogen atom, or other cations derived from metals, the benzenesulfonic acid salts of which being water-soluble; $m_1$, $m_2$ and $m_3$ are integers, which may be identical or different, ranging from 0 to 5; and $n_1$, $n_2$ and $n_3$ are integers, which may be identical or different, ranging from 0 to 3, at least one of these being equal to or greater than 1; and (b) of at least one transition metal compound.

DETAILED DESCRIPTION OF BEST MODE AND PREFERRED EMBODIMENTS OF THE INVENTION

More particularly according to the present invention, exemplary metals, the benzenesulfonic acid salts thereof being water-soluble, include lead, zinc and tin.

By the expression "water-soluble" is intended a compound which has a solubility of at least 0.01 g per liter of water.

Exemplary preferred phosphines of formula (I) include those in which $Ar_1$, $Ar_2$ and $Ar_3$ are phenyl radicals; $Y_1$, $Y_2$ and $Y_3$ are each alkyl radicals having from 1 to 2 carbon atoms, or alkoxy radicals having from 1 to 2 carbon atoms; M is a cation selected from among $H^+$, cations derived from Na, K, Ca and Ba, $NH_4^+$, or tetramethylammonium, tetraethylammonium, tetrapropylammonium and tetrabutylammonium cations; $m_1$, $m_2$ and $m_3$ are integers ranging from 0 to 3; and $n_1$, $n_2$ and $n_3$ are integers ranging from 0 to 3, at least one of which being greater than 1.

Among these phosphines, the sodium, potassium, calcium, barium, ammonium, tetramethylammonium and tetraethylammonium salts of mono(sulfophenyl)-diphenylphosphine, di(sulfophenyl)-phenylphosphine and tri(sulfophenyl)phosphine, in which the $SO_3$ groups are preferably in the meta-position, are more particularly preferred.

Other phosphines of formula (I) which may be used in the process of the invention include the alkali metal or alkaline earth metal salts; ammonium salts; quaternary ammonium salts of (3-sulfo-4-methylphenyl)di(4-methylphenyl) phosphine, (3-sulfo-4-methoxyphenyl)-di(4-methoxyphenyl)phosphine, (3-sulfo-4-chlorophenyl)-di(4-chlorophenyl)phosphine, di(3-sulfophenyl)phenylphosphine, di(4-sulfophenyl)-phenylphosphine, di(3-sulfo-4-methylphenyl)

(4-methylphenyl)phosphine, di(3-sulfo-4-methoxyphenyl) (4-methoxyphenyl)phosphine, di(3-sulfo-4-chlorophenyl) (4-chlorophenyl)phosphine, tri(3-sulfophenyl)phosphine, tri(4-sulfophenyl)phosphine, tri(3-sulfo-4-methylphenyl)phosphine, tri(3-sulfo-4-methoxyphenyl)phosphine, tri(3-sulfo-4-chlorophenyl)phosphine, (2-sulfo-4-methylphenyl) (3-sulfo-4-methylphenyl) (3,5-disulfo-4-methylphenyl)phosphine, (3-sulfophenyl) (3-sulfo-4-chlorophenyl) (3,5-disulfo-4-chlorophenyl)phosphine.

It is, of course, also possible to employ a mixture of these phosphines. In particular, a mixture of mono-, di- and tri-meta-sulfonated phosphines may be used.

Compounds of nickel, of palladium and of iron are the preferred transition metal compounds. Water-soluble compounds or compounds that dissolve under the conditions of reaction are used. The residue bonded to the metal is not critical, as long as it satisfies these conditions.

Among such compounds, those of nickel are the preferred. Exemplary thereof are compounds in which the nickel is in the oxidation state of zero, e.g., potassium tetracyanonickelate $K_4(NiCN_4)$, bis (acrylonitrile) nickel, bis (1,5-cyclooctadiene) nickel and derivatives containing ligands from Group Va of the Periodic Table, e.g., tetrakis (triphenylphosphine)nickel (in the latter instance the compound may be dissolved in a water-immiscible solvent such as toluene, and then treated with an aqueous solution of sulfonated phosphine which extracts some of the nickel by developing a red coloration in the aqueous solution which separates out on settling); and compounds of nickel in an oxidation state greater than 0, e.g., carboxylates (in particular acetate), carbonate, bicarbonate, borate, bromide, chloride, citrate, thiocyanate, cyanide, formate, hydroxide, hydrophosphite, phosphite, phosphate and derivatives thereof, iodide, nitrate, sulfate, sulfite, arylsulfonates and alkylsulfonates.

It is not necessary that the nickel compound itself be water-soluble. For example, nickel cyanide, which is sparingly soluble in water, is very soluble in an aqueous solution of phosphine.

When the nickel compound exhibits a nickel oxidation state greater than 0, a nickel-reducing agent which reacts preferentially with nickel under the conditions of reaction is added to the reaction medium. This reducing agent may be organic or inorganic. Exemplary thereof are $NaBH_4$, Zn powder, magnesium, $KBH_4$ and borohydrides which are preferably water-soluble.

This reducing agent is added in an amount such that the number of redox equivalents ranges from 1 to 10. However, values of less than 1 and greater than 10 are also within the ambit of the present invention.

When the nickel compound corresponds to the 0 oxidation state of nickel, a reducing agent of the type of those indicated above may also be added, but this is not essential.

When an iron compound is used, the same reducing agents are suitable.

In the case of palladium, the reducing agents may additionally be components of the reaction medium (phosphine, solvent or olefin).

The sulfonated phosphines used in the process according to the present invention may be prepared via known processes. Thus, in accordance with H. Schindlbauer, *Monatsch. Chem.*, 96, pages 2051–2057 (1965), the sodium salt of (p-sulfophenyl)diphenylphosphine may be prepared by reacting sodium p-chlorobenzenesulfonate with diphenylchlorophosphine, in the presence of sodium or potassium.

According to the technique described in *J. Chem. Soc.*, pages 276–288 (1958) and in GB-1,066,261, phenylphosphines of formula (I) may be prepared by the sulfonation of aromatic ring-systems using oleum, followed by neutralization of the sulfonic groups formed by means of a suitable basic derivative of one of the metals represented by M in the formula (I). The crude sulfonated phosphine obtained may contain, as a mixture, the corresponding sulfonated phosphine oxide, the presence of which does not, however, adversely affect the isomerization process according to the present invention.

The 2-methyl-3-butenenitrile subjected to isomerization according to this invention may be used alone, or in admixture with other compounds.

Thus, 2-methyl-3-butenenitrile may be employed in admixture with 2-methyl-2-butenenitrile, 4-pentenenitrile, 3-pentenenitrile, 2-pentenenitrile, butadiene, adiponitrile, 2-methylglutaronitrile, 2-ethylsuccinonitrile, or valeronitrile.

Hence, one particularly advantageous embodiment of this invention entails treating the reaction mixture obtained from the hydrocyanation of butadiene with HCN in the presence of an aqueous solution of a sulfonated phosphine of formula (I) and of a transition metal compound, more preferably a compound of nickel of oxidation state 0, as described above.

In this preferred embodiment, since the catalytic system is already present for the hydrocyanation reaction of butadiene, it is sufficient to cease introduction of the hydrocyanic acid for the isomerization reaction to occur.

If necessary, it is possible in this embodiment to flush the reactor gently with an inert gas such as nitrogen or argon, for example, in order to expel the hydrocyanic acid which may still be present.

The isomerization reaction is generally carried out at a temperature of from 10° C. to 150° C. and preferably of 60° C. to 120° C.

In the case of an isomerization immediately following the hydrocyanation of butadiene, it will be advantageous to conduct the reaction at the temperature at which the hydrocyanation was carried out.

The catalytic solution used for the isomerization according to the invention may be prepared before its introduction into the reaction zone, for example by addition to the aqueous solution of the phosphine of formula (I), the appropriate amount of the transition metal compound selected and optionally of the reducing agent. It is also possible to prepare the catalytic solution "in situ" simply by mixing these various constituents.

The amount of nickel compound used is selected such that there exists from $10^{-4}$ to 1 and preferably from 0.005 to 0.5 mol of nickel per liter of reaction solution.

The amount of phosphine of formula (I) used to prepare the reaction solution is selected such that the number of moles of this compound relative to 1 mol of elemental metal ranges from 0.5 to 2,000 and preferably from 2 to 300.

Although the reaction is generally carried out in the absence of a third solvent, it may be advantageous to add an inert, water-immiscible organic solvent, which may be that of the subsequent extraction.

Exemplary such solvents include the aromatic, aliphatic or cycloaliphatic hydrocarbons which maintain the reaction medium in the two-phase state.

Thus, once the reaction has been completed, it is very simple to separate, on the one hand, an aqueous phase containing the sulfonated phosphine of formula (I) and the transition metal compound and, on the other, an organic phase comprising the reactants employed in the reaction, the reaction products and, where appropriate, the water-immiscible organic solvent.

Exemplary organic solvents which may be used in the isomerization process include benzene, toluene, xylenes, hexane and cyclohexane.

In order to further illustrate the present invention and the advantages thereof, the following specific examples are given, it being understood that same are intended only as illustrative and in nowise limitative.

EXAMPLE 1

(1) Preparation of a Ni/TSTPP catalytic solution:

500 cm³ of a solution of 350 mmol of the sodium salt of trisulfonated triphenylphosphine (TSTPP) in water were charged into a 1-liter glass round-bottomed flask fitted with a magnetic stirring bar and an ascending condenser; this solution was degassed. Next, 19.20 g (70 mmol) of Ni(cyclooctadiene)$_2$ were introduced, followed by 350 cm³ of previously degassed orthoxylene, with stirring and under a stream of argon.

The mixture was heated at 45° C. for 15 h. After cooling, the two-phase system was allowed to separate by settling and the strongly red-colored aqueous phase was withdrawn.

(2) Isomerization of 2-methyl-3-butenenitrile:

The following materials were charged into a 150 cm³ glass reactor stirred using a turbine:

(i) 2-methyl-3-butenenitrile (2M3BN): 48.6 g (600 mmol), (ii) aqueous solution containing 0.14 mol/l of Ni and 0.7 mol/l of the sodium salt of trisulfonated triphenylphosphine (TSTPP): 16 cm³ (equivalent to 2.24 mmol of Ni and 11.2 mmol of TSTPP).

The reaction mixture was stirred for 1.5 h at 90° C.

After cooling and separation of the phases by settling, the final organic phase was assayed by gas chromatography (GC).

The following results were obtained:

(a) Extent of conversion (EC) of 2M3BN: 95%, (b) Yield (Yd) of 3-pentenenitrile (3PN) relative to the 2M3BN converted: 91.5%, (c) Yield (Yd) of 2-methyl-2-butenenitrile (2M2BN) relative to the 2M3BN converted: 8%.

EXAMPLE 2

In situ reduction of Ni (II):

The following reagents were charged into the apparatus described in Example 1:

| | | |
|---|---|---|
| (i) NiCl$_2$ | 0.75 mmol | |
| (ii) TSTPP | 3.15 mmol | |
| (iii) NaBH$_4$ | 0.8 mmol | |
| (iv) H$_2$O | 2.8 g | |
| (v) 2M3BN | 200 mmol | |

The mixture was reacted with stirring for 3 h at 110° C.
The organic phase was assayed by GC.
The following results were obtained:

| | | |
|---|---|---|
| (a) EC of 2M3BN | 64% | |
| (b) Yd of 3PN | 97% | |
| (c) Yd of 2M2BN | 3% | |

EXAMPLE 3

The procedure of Example 2 was repeated using the following charges:

| | | |
|---|---|---|
| (i) Ni(Cod)$_2$ (Cod = cyclooctadiene) | 0.75 mmol | |
| (ii) TSTPP | 3.4 mmol | |
| (iii) H$_2$O | 3.8 g | |
| (iv) 2M3BN | 200 mmol | |

Temperature: 90° C.
Time: 2 h
The following results were obtained:

| | | |
|---|---|---|
| (a) EC of 2M3BN | 87% | |
| (b) Yd of 3PN | 93% | |
| (c) Yd of 2M2BN | 2% | |

EXAMPLE 4

The procedure of Example 2 was repeated using the following charges:

| | | |
|---|---|---|
| (i) Ni(Cod)$_2$ | 0.75 mmol | |
| (ii) TSTPP | 3.15 mmol | |
| (iii) H$_2$O | 2.8 g | |
| (iv) 2M3BN | 200 mmol | |

Temperature: 110° C.
Time: 0.25 h and 0.5 h
The following results were obtained:

TABLE 1

| | For 0.25 h | For 0.5 h |
|---|---|---|
| EC of 2M3BN | 75% | 87% |
| Yd of 3PN | 92% | 94% |
| Yd of 2M2BN | 5% | 5% |

EXAMPLE 5

The procedure of Example 2 was repeated using the following charges:

| | | |
|---|---|---|
| (i) NI(Cod)$_2$ | 2.5 mmol | |
| (ii) TSTPP | 10.8 mmol | |
| (iii) H$_2$O | 5 g | |
| (iv) 2M3BN | 200 mmol | |

Temperature: 56° C.
Time: 4 h
The following results were obtained:

| | | |
|---|---|---|
| (a) EC of 2M3BN | 87% | |
| (b) Yd of 3PN | 94% | |

EXAMPLES 6 TO 8

The procedure of Example 2 was repeated using the following charges:

| | | |
|---|---|---|
| (i) | Ni(Cod)₂ | 0.7 mmol |
| (ii) | TSTPP | see Table 2 |
| (iii) | H₂O | 5 g |
| (iv) | 2M3BN | 200 mmol (20 cm³) |

Temperature: 90° C.
Time: see Table 2
The results obtained are reported in Table 2 below:

TABLE 2

| Examples | TSTPP mmol | Time | EC of 2M3BN | Yd of 3PN | Yd of 2M2BN |
|---|---|---|---|---|---|
| Example 6 | 2.15 | 0.5 h | 39% | 80% | 15% |
| | | 1.5 h | 81% | 88% | 12% |
| Example 7 | 3.6 | 0.5 h | 45% | 89% | 9% |
| | | 1.5 h | 87% | 92% | 7% |
| Example 8 | 5.4 | 0.5 h | 49% | 92% | 6% |
| | | 1.5 h | 62% | 92% | 6% |

EXAMPLES 9 AND 10

The procedure of Example 2 was repeated using the following charges:

| | | |
|---|---|---|
| (i) | Ni(Cod)₂ | see Table 3 |
| (ii) | TSTPP | 10.5 mmol |
| (iii) | H₂O | 15 g |
| (iv) | 2M3BN | 600 mmol (60 cm³) |

Temperature: 90° C.
Time: see Table 3
The results obtained are reported in Table 3 below:

TABLE 3

| Examples | Ni(Cod)₂ mmol | Time | EC of 2M3BN | Yd of 3PN | Yd of 2M2BN |
|---|---|---|---|---|---|
| Example 9 | 0.3 | 0.5 h | 11% | 66% | 33% |
| | | 1.5 h | 28% | 66% | 33% |
| Example 10 | 2.85 | 0.5 h | 48% | 93% | 6% |
| | | 1.5 h | 94% | 93% | 6% |

EXAMPLE 11

Recycling tests:

The procedure of Example 2 was repeated, but after the test the organic phase was separated and assayed by GC, while the organic phase containing the nickel catalyst and the TSTPP was recycled with a new charge of 2M3BN.

The following compounds were charged:

| | | |
|---|---|---|
| (i) | Ni(Cod)₂ | 0.74 mmol |
| (ii) | TSTPP | 3.4 mmol |
| (iii) | H₂O | 3.8 g |
| (iv) | 2M3BN | see Table 4 |

Temperature: 90° C.
Time: 90 min for each test
The results obtained are reported in Table 4 below:

TABLE 4

| Recycling | 2M3BN charged (mmol) | EC of 2M3BN | Yd of 3PN | Yd of 2M2BN |
|---|---|---|---|---|
| 0 | 211 | 93% | 92% | 5% |
| 1 | 205 | 78% | 96% | 4% |
| 2 | 225 | 60% | 90% | 5% |

EXAMPLE 12

Recycling tests:

The procedure of Example 11 was repeated using the following charges:

| | | |
|---|---|---|
| (i) | Ni(Cod)₂ | 2.26 mmol |
| (ii) | TSTPP | 10.1 mmol |
| (iii) | H₂O | 16 g |
| (iv) | 2M3BN | see Table 5 |

Temperature: 90° C.
Time: see Table 5
The results obtained are reported in Table 5 below:

TABLE 5

| Recycling | 2M3BN charged (mmol) | Time (min) | EC of 2M3BN | Yd of 3PN | Yd of 2M2BN |
|---|---|---|---|---|---|
| 0 | 600 | 90 | 95% | 91% | 8% |
| 1 | 600 | 90 | 73% | 90% | 9% |
| 2 | 600 | 90 | 47% | 90% | 9% |
| | | 180 | 72% | 90% | 9% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the conversion of 2-methyl-3-butenenitrile into a linear pentenenitrile, comprising isomerizing said 2-methyl-3-butenenitrile in the presence of a catalytically effective amount of an aqueous solution which comprises:

(a) at least one sulfonated phosphine of the general formula (I):

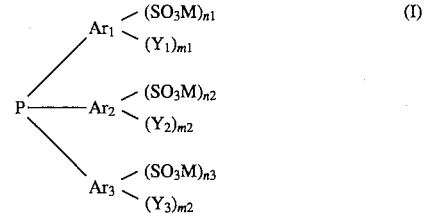

in which $Ar_1$, $Ar_2$ and $Ar_3$, which may be identical or different, are each an aryl radical; $Y_1$, $Y_2$ and $Y_3$, which may be identical or different, are each an alkyl radical having from 1 to 4 carbon atoms, an alkoxy radical having from 1 to 4 carbon atoms, a halogen atom, a CN radical, an $NO_2$ radical, an OH radical, or a radical $NR_1R_2$, in which $R_1$ and $R_2$, which may be identical or different, are each an alkyl radical having from 1 to 4 carbon atoms; M is an inorganic or organic cation selected such that the compound of formula (I) is water-soluble, from among $H^+$, cations derived from alkali metals or alkaline earth metals, $N(R_3R_4R_5R_6)_+$ in which $R_3$, $R_4$, $R_5$ and $R_6$, which may be identical or different are each an alkyl radical having from 1 to 4 carbon atoms, or a hydrogen atom, or other cations derived from metals, the benzenesulfonic acid salts thereof being water-soluble; $m_1$, $m_2$ and $m_3$ are integers, which may be identical or different, ranging from 0 to 5; and $n_1$, $n_2$ and $n_3$ are integers, which may be identical or different, ranging from 0 to 3, at least one of which being equal to or greater than 1; and (b) at least one transition metal compound; to yield a product containing at least 66% by weight of a linear pentenenitrile.

2. The process as defined by claim 1, wherein said at least one sulfonated phosphine of general formula (I), $Ar_1$, $Ar_2$ and $Ar_3$ are phenyl radicals; $Y_1$, $Y_2$ and $Y_3$ are each alkyl radicals having from 1 to 2 carbon atoms, or alkoxy radicals having from 1 to 2 carbon atoms; M is a cation selected from among $H^+$, cations derived from Na, K, Ca and Ba, $NH_4^+$, or tetramethylammonium, tetraethylammonium, tetrapropylammonium and tetrabutylammonium cations; $m_1$, $m_2$ and $m_3$ are integers ranging from 0 to 3; and $n_1$, $n_2$ and $n_3$ are integers ranging from 0 to 3, at least one of which being greater than 1.

3. The process as defined by claim 1, said at least one sulfonated phosphine of general formula (I) comprising a sodium, potassium, calcium, barium, ammonium, tetramethylammonium or tetraethylammonium salt of mono(sulfophenyl)diphenylphosphine, di(sulfophenyl)phenylphosphine or tri(sulfophenyl)phosphine.

4. The process as defined by claim 3, the $SO_3$ groups of said at least one sulfonated phosphine being in the meta-position.

5. The process as defined by claim 1, said at least one transition metal compound comprising a compound of nickel, palladium, or iron.

6. The process as defined by claim 5, said at least one transition metal compound comprising a nickel compound, the nickel values of which being in an oxidation state of zero.

7. The process as defined by claim 5, said at least one transition metal compound comprising a nickel compound, the nickel values of which being in an oxidation state greater than zero.

8. The process as defined by claim 5, the medium of isomerization also comprising a nickel-reducing agent.

9. The process as defined by claim 8, the number of redox equivalents of said nickel-reducing agent ranging from 1 to 10.

10. The process as defined by claim 1, said starting material 2-methyl-3-butenenitrile comprising admixture thereof with 2-methyl-2-butenenitrile, 4-pentenenitrile, 3-pentenenitrile, 2-pentenenitrile, butadiene, adiponitrile, 2-methylglutaronitrile, 2-ethylsuccinonitrile, or valeronitrile.

11. The process as defined by claim 1, comprising isomerizing the reaction mixture obtained via the hydrocyanation of butadiene with HCN.

12. The process as defined by claim 1, carried out at a temperature ranging from 10° to 150° C.

13. The process as defined by claim 12, carried out at a temperature ranging from 60° to 120° C.

14. The process as defined by claim 1, said at least one transition metal compound comprising a compound of nickel, the amount of which ranging from $10^{-4}$ to 1 mol of nickel per liter of medium of isomerization.

15. The process as defined by claim 14, said amount ranging from 0.005 to 0.5 mol of nickel per liter of medium of isomerization.

16. The process as defined by claim 1, the ratio of the amount of said at least one sulfonated phosphine per 1 mol of elemental metal comprising said at least one transition metal compound ranging from 0.5 to 2,000.

17. The process as defined by claim 16, said ratio ranging from 2 to 300.

18. The process as defined by claim 1, the medium of isomerization also comprising an inert, water-immiscible organic solvent.

* * * * *